United States Patent
Hlopick et al.

(10) Patent No.: US 11,090,456 B2
(45) Date of Patent: Aug. 17, 2021

(54) LIQUID REMOVAL IN A PATIENT INTERFACE ASSEMBLY

(71) Applicant: KONINKLIJKE PHILIPS N.V., Eindhoven (NL)

(72) Inventors: Stephen George Hlopick, Murrysville, PA (US); Richard Thomas Haibach, Verona, PA (US); Robert Earl Hieber, Export, PA (US)

(73) Assignee: Koninklijke Philips N.V., Eindhoven (NL)

( * ) Notice: Subject to any disclaimer, the term of this patent is extended or adjusted under 35 U.S.C. 154(b) by 340 days.

(21) Appl. No.: 15/572,173

(22) PCT Filed: Apr. 27, 2016

(86) PCT No.: PCT/IB2016/052369
§ 371 (c)(1),
(2) Date: Nov. 7, 2017

(87) PCT Pub. No.: WO2016/181246
PCT Pub. Date: Nov. 17, 2016

(65) Prior Publication Data
US 2018/0147382 A1   May 31, 2018

Related U.S. Application Data

(60) Provisional application No. 62/158,869, filed on May 8, 2015.

(51) Int. Cl.
*A61M 16/08* (2006.01)
*A61M 16/06* (2006.01)
*A61M 16/00* (2006.01)

(52) U.S. Cl.
CPC .... *A61M 16/0808* (2013.01); *A61M 16/0057* (2013.01); *A61M 16/06* (2013.01);
(Continued)

(58) Field of Classification Search
CPC .......... A61M 16/0808; A61M 16/0816; A61M 16/0683; A61M 16/0672; A61M 16/0666;
(Continued)

(56) References Cited

U.S. PATENT DOCUMENTS 3,454,005 A   7/1969  Eubanks
4,570,639 A * 2/1986  Miodownik ........... A61B 5/083
                                              340/608
(Continued)

FOREIGN PATENT DOCUMENTS

CN      102302817 A    1/2012
WO   WO20121063737 A2  8/2012
(Continued)

*Primary Examiner* — Jan Christopher L Merene
*Assistant Examiner* — Brian T Khong
(74) *Attorney, Agent, or Firm* — Michael W. Haas (57) ABSTRACT

A patient interface device is for a pressure support system that includes a flow generator that produces a flow of breathing gas to be delivered to an airway of a patient. The patient interface device includes a sealing element to engage a face of the patient and receive the flow of breathing gas; a lumen having a first end and a second end opposite and distal the first end, the first end being in fluid communication with an interior of the sealing element; a connector member coupled to the second end of the lumen; a pressure sensor coupled to the connector member, the pressure sensor sensing pressure of a gas exiting the second end of the lumen; and a surface provided on one of the lumen and the connector member, the surface defining a thru hole through which undesirable liquid in the lumen can escape.

12 Claims, 11 Drawing Sheets

(52) U.S. Cl.
CPC .... *A61M 16/0605* (2014.02); *A61M 16/0683* (2013.01); *A61M 16/08* (2013.01); *A61M 16/0816* (2013.01); *A61M 16/0858* (2014.02); *A61M 2016/0027* (2013.01)

(58) Field of Classification Search
CPC .............. A61M 16/0605; A61M 16/06; A61M 16/0858; A61M 16/085; A61M 16/0057; A61M 16/0054; A61M 16/08; A61M 16/0841; A61M 16/0875; A61M 2016/0027; A61M 2016/0015; A61M 2016/102; A61M 2016/0036; A61M 2016/0039; A61M 2016/0042; A61M 5/365; A61B 5/087; A61B 2562/0247
See application file for complete search history.

(56) References Cited

U.S. PATENT DOCUMENTS

| | | | |
|---|---|---|---|
| 4,592,368 A * | 6/1986 | Ricciardelli | G01N 33/497 128/205.12 |
| 5,398,677 A | 3/1995 | Smith | |
| 6,279,574 B1 * | 8/2001 | Richardson | A61M 16/0096 128/204.18 |
| 7,530,353 B2 | 5/2009 | Choncholas | |
| 7,554,666 B2 | 6/2009 | Russell | |
| 8,844,533 B2 | 9/2014 | Allum | |
| 8,925,545 B2 | 1/2015 | Wondka | |
| 2002/0162397 A1 * | 11/2002 | Orr | A61B 5/087 73/700 |
| 2004/0193100 A1 * | 9/2004 | Van Hooser | A61M 16/0808 604/35 |
| 2004/0193101 A1 * | 9/2004 | Van Hooser | A61M 16/0808 604/35 |
| 2007/0193580 A1 * | 8/2007 | Feldhahn | A61M 16/0051 128/204.18 |
| 2007/0225612 A1 * | 9/2007 | Mace | A61B 5/083 600/532 |
| 2007/0273887 A1 * | 11/2007 | Russell | A61M 16/08 356/450 |
| 2008/0078388 A1 * | 4/2008 | Vandine | A61M 16/04 128/204.21 |
| 2008/0127977 A1 * | 6/2008 | Orr | A61B 5/0833 128/204.22 |
| 2008/0283062 A1 * | 11/2008 | Esposito, Jr. | A61B 5/061 128/204.23 |
| 2010/0036272 A1 * | 2/2010 | Mace | A61B 5/083 600/531 |
| 2010/0168599 A1 * | 7/2010 | Esposito | A61B 5/061 600/532 |
| 2010/0170513 A1 * | 7/2010 | Bowditch | A61M 16/0066 128/204.23 |
| 2011/0067699 A1 * | 3/2011 | Caruso | A61M 16/0427 128/205.29 |
| 2011/0130741 A1 * | 6/2011 | Miles | G01N 29/032 604/500 |
| 2011/0144514 A1 * | 6/2011 | Booker | A61M 16/0475 600/529 |
| 2011/0209703 A1 | 9/2011 | Usuda | |
| 2011/0284001 A1 * | 11/2011 | Tero | A61M 16/0009 128/204.18 |
| 2012/0097156 A1 * | 4/2012 | Bowman | A61M 16/06 128/201.13 |
| 2012/0152255 A1 * | 6/2012 | Barlow | A61M 16/0066 128/205.25 |
| 2012/0167879 A1 * | 7/2012 | Bowman | A61M 16/0066 128/201.22 |
| 2012/0325219 A1 | 12/2012 | Smith | |
| 2013/0098359 A1 * | 4/2013 | Becker | A61M 16/0666 128/201.13 |
| 2013/0291871 A1 * | 11/2013 | Wood | A61M 16/0445 128/207.15 |
| 2014/0243797 A1 * | 8/2014 | Jensen | A61M 39/1011 604/535 |
| 2014/0318546 A1 | 10/2014 | Haibach | |
| 2014/0330154 A1 * | 11/2014 | Haveri | A61B 5/083 600/532 |
| 2014/0373835 A1 * | 12/2014 | Ahmad | A61M 16/0875 128/203.12 |
| 2015/0040895 A1 * | 2/2015 | Niland | A61M 16/0875 128/202.16 |
| 2015/0083126 A1 * | 3/2015 | Rogers | A61M 16/164 128/203.14 |
| 2015/0157818 A1 * | 6/2015 | Darby | A61M 16/0066 128/201.13 |
| 2015/0223728 A1 * | 8/2015 | Fudge | A61B 5/097 600/532 |
| 2015/0283351 A1 | 10/2015 | Castello | |
| 2015/0320962 A1 * | 11/2015 | Bafile | A61M 16/0816 128/204.18 |
| 2016/0015916 A1 * | 1/2016 | Goff | A61M 16/0683 128/205.12 |
| 2016/0067430 A1 * | 3/2016 | Lin | A61M 16/0816 128/202.27 |
| 2016/0151597 A1 * | 6/2016 | Baecke | A61M 16/0611 128/204.21 |
| 2016/0151741 A1 * | 6/2016 | Zhu | A61M 16/085 95/22 |
| 2017/0074695 A1 * | 3/2017 | Baecke | G01L 13/00 |

FOREIGN PATENT DOCUMENTS

| | | |
|---|---|---|
| WO | WO2012177562 A1 | 12/2012 |
| WO | WO2014025591 A1 | 2/2014 |
| WO | WO2014138125 A1 | 9/2014 |

\* cited by examiner

LIQUID REMOVAL IN A PATIENT INTERFACE ASSEMBLY

CROSS-REFERENCE TO RELATED APPLICATIONS

This patent application claims the priority benefit under 35 U.S.C. § 371 of international patent application no. PCT/IB2016/052369, filed Apr. 27, 2016, which claims the priority benefit under 35 U.S.C. § 119(e) of U.S. Provisional Application No. 62/158,869, filed on May 8, 2015, the contents of which are herein incorporated by reference.

BACKGROUND OF THE INVENTION

1. Field of the Invention

The present invention relates to non-invasive ventilation and pressure support systems in which a patient interface device is used to deliver a flow of breathing gas to a patient. The present invention also relates to methods of removing undesirable liquid in patient interface devices.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery hose and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Furthermore, it is desired to sense pressure within the patient interface device at a location near the patient airway in order to more accurately deliver therapy. One method to sense pressure is to use a small lumen tube to transfer the pressure from a location close to the patient airway to a location where it is suitable to place a pressure sensor, without size constraints. A significant drawback with such a method is that if liquid enters the lumen tube, such as during cleaning of the patient interface device, pressure accuracy is jeopardized.

SUMMARY OF THE INVENTION

As one aspect of the disclosed concept, a patient interface device for a pressure support system is provided. The pressure support system includes a gas flow generator structured to produce a flow of breathing gas to be delivered to an airway of a patient. The patient interface device comprises: a sealing element structured to engage a face of the patient and to receive the flow of breathing gas; a lumen having a first end and a second end opposite and distal the first end, the first end being in fluid communication with an interior of the sealing element; a connector member coupled to the second end of the lumen; a pressure sensor coupled to the connector member, the pressure sensor being structured to sense pressure of a gas exiting the second end of the lumen; and a surface provided on one of the lumen and the connector member, the surface defining a thru hole through which undesirable liquid in the lumen can escape.

As another aspect of the disclosed concept, a pressure support system comprises: a gas flow generator structured to produce a flow of breathing gas to be delivered to an airway of a patient; and a patient interface device.

As another aspect of the disclosed concept, a method of removing undesirable liquid in a patient interface device comprises the steps of: producing a flow of breathing gas to be delivered to an airway of a patient with a gas flow generator; and forcing undesirable liquid in a lumen through a thru hole with a portion of the gas exiting a second end of the lumen.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
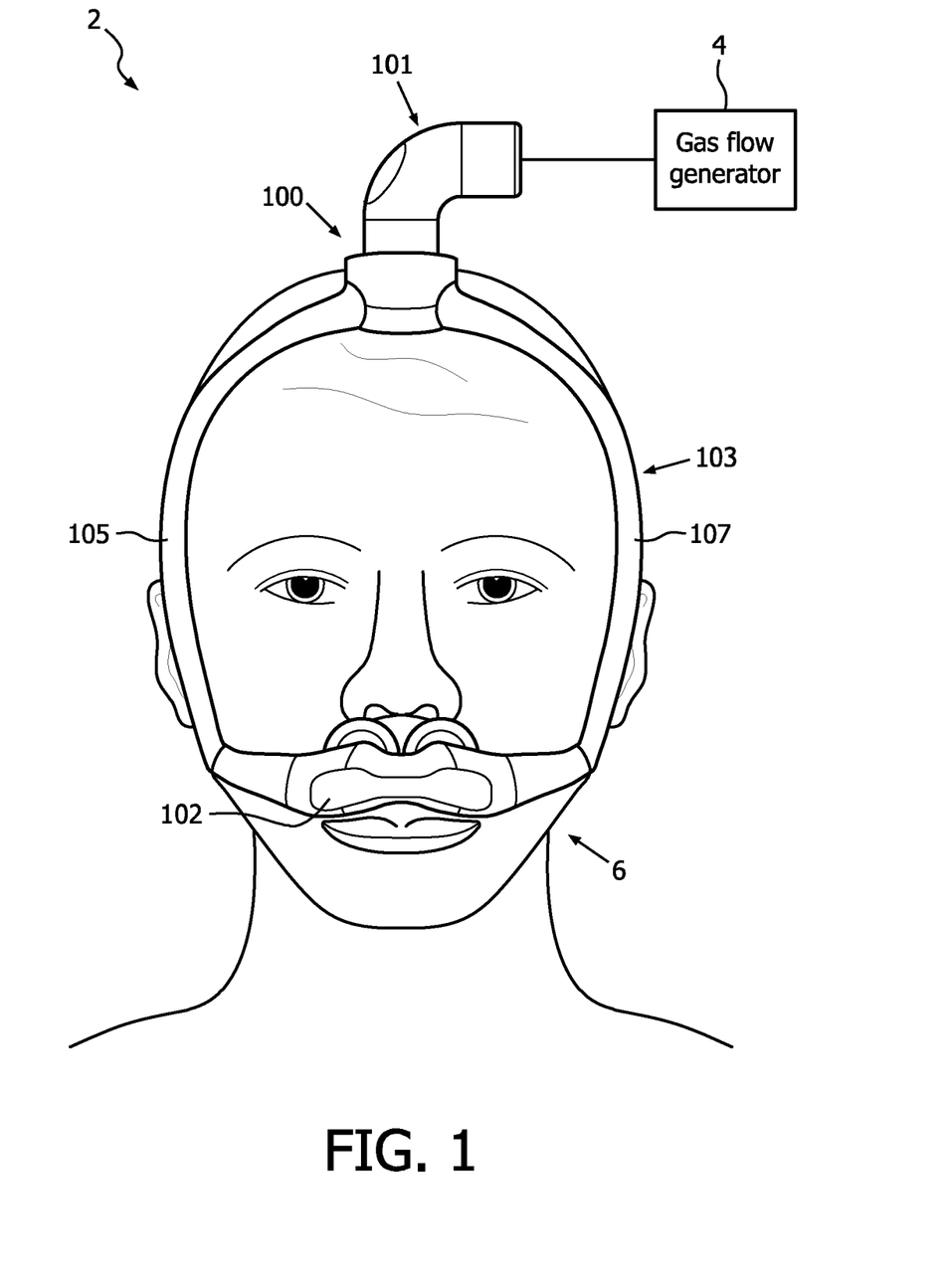
FIG. 1 is a simplified view of a pressure support system and patient interface device therefor, shown as employed on a patient, in accordance with a non-limiting embodiment of the disclosed concept.

FIG. 1 is a simplified view of a pressure support system 2 in accordance with a non-limiting embodiment of the disclosed concept. Pressure support system 2 includes a gas flow generator 4 (shown in simplified form) that produces a flow of breathing gas to be delivered to an airway of a patient 6, and a patient interface device 100 fluidly coupled to gas flow generator 4. Patient interface device 100 has a sealing element 102 that engages a face of patient 6 and receives the flow of breathing gas generated by gas flow generator 4 in order that the breathing gas can be delivered to the airway of patient 6. As will be discussed in greater detail herein below, patient interface device 100 advantageously allows undesirable liquid located therein to be removed so that pressure sensor readings can be more accurate, resulting in better monitoring of, and therefore improved delivery of, pressure support therapy.

Figure 2:
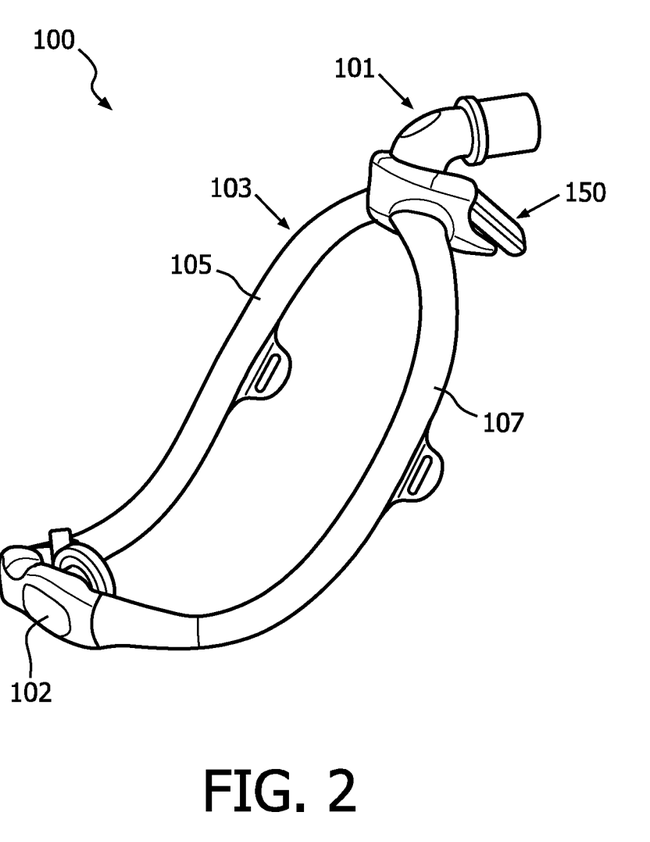
FIG. 2 is a front isometric view of the patient interface device of FIG. 1.

FIG. 2 shows an isometric view of patient interface device 100. As shown, patient interface device 100 further includes a fluid coupling conduit (i.e., elbow connector 101) and a delivery tube apparatus 103 fluidly coupled to elbow connector 101. Delivery tube apparatus 103 has a first delivery tube 105 and a second delivery tube 107 each fluidly coupled to elbow connector 101 and sealing element 102. Referring again to FIG. 1, delivery tubes 105,107 each extend along opposing sides of the face of patient 6. Thus, it will be appreciated that elbow connector 101 is structured to communicate the flow of breathing gas from gas flow generator 4 to sealing element 102 (i.e., and as a result the airway of patient 6) through delivery tubes 105,107.

Figures 3, 4:
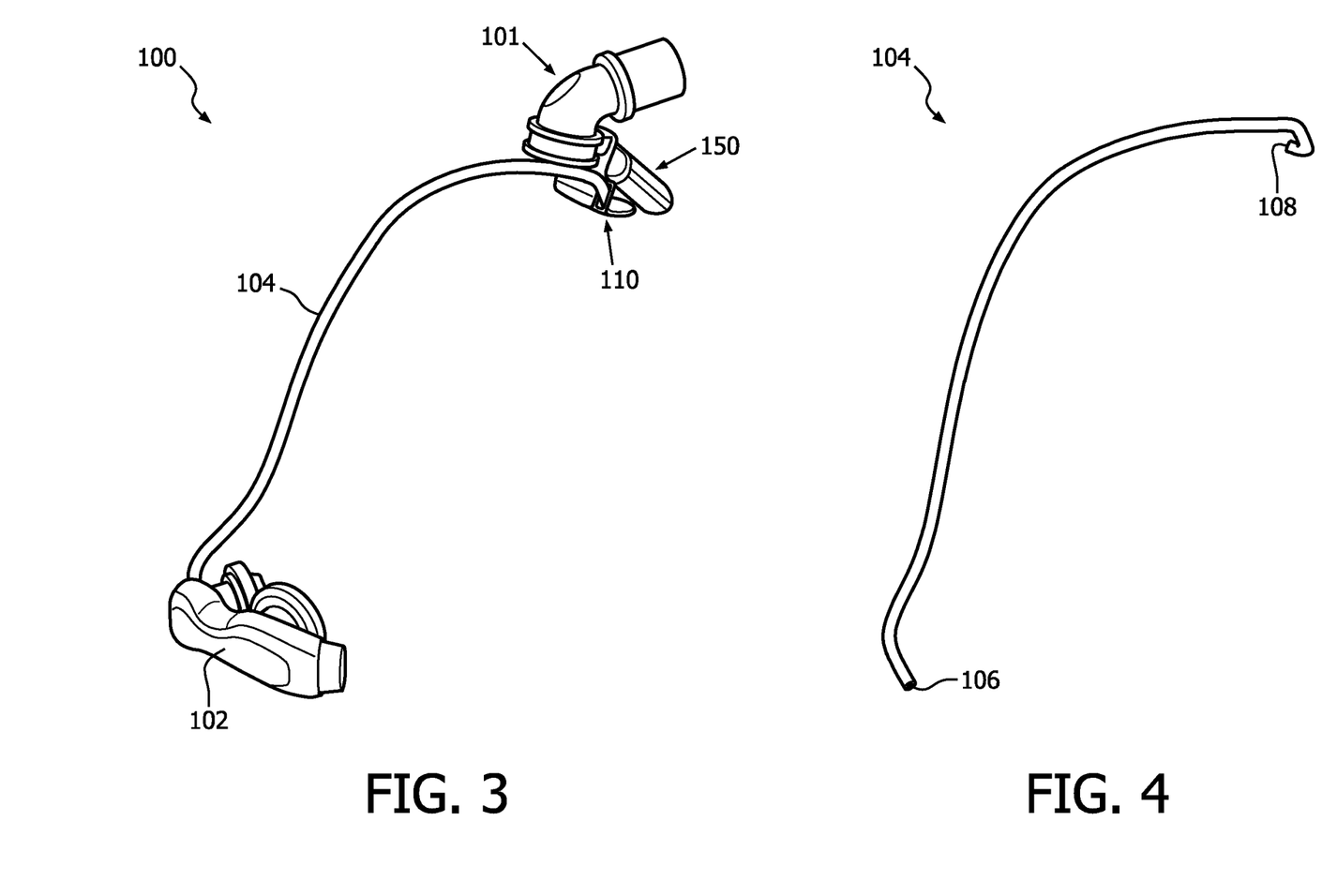
FIG. 3 is another front isometric view of the patient interface device of FIG. 1, and shown with a portion of the patient interface device removed in order to see hidden features.
FIG. 4 is a front isometric view of a lumen for the patient interface device of FIG. 1.

FIG. 3 shows another isometric view of patient interface device 100, with a portion removed. As shown in FIG. 3, patient interface device 100 further has a pressure lumen 104, a connector member 110, and a pressure sensor 150. In the depicted embodiment, lumen 104 is located inside (i.e., is enclosed by and/or is substantially internal with respect to) delivery tube 105 (FIG. 1 and FIG. 2). It will however be appreciated that lumen 104, or a suitable alternative lumen (i.e., lumen 104', discussed herein below), may be located in a different location (e.g., without limitation, partially inside and partially outside the delivery tube apparatus 103 (not shown)), without departing from the scope of the disclosed concept.

Referring to FIG. 4, lumen 104 has a first end 106 and a second end 108 located opposite and distal first end 106. Connector member 110 is connected to both second end 108 of lumen 104, and pressure sensor 150, and allows gas exiting second end 108 of lumen 104 to pass to pressure sensor 150 in order that pressure readings may be taken for pressure support system 2 (FIG. 1).

Figure 5:
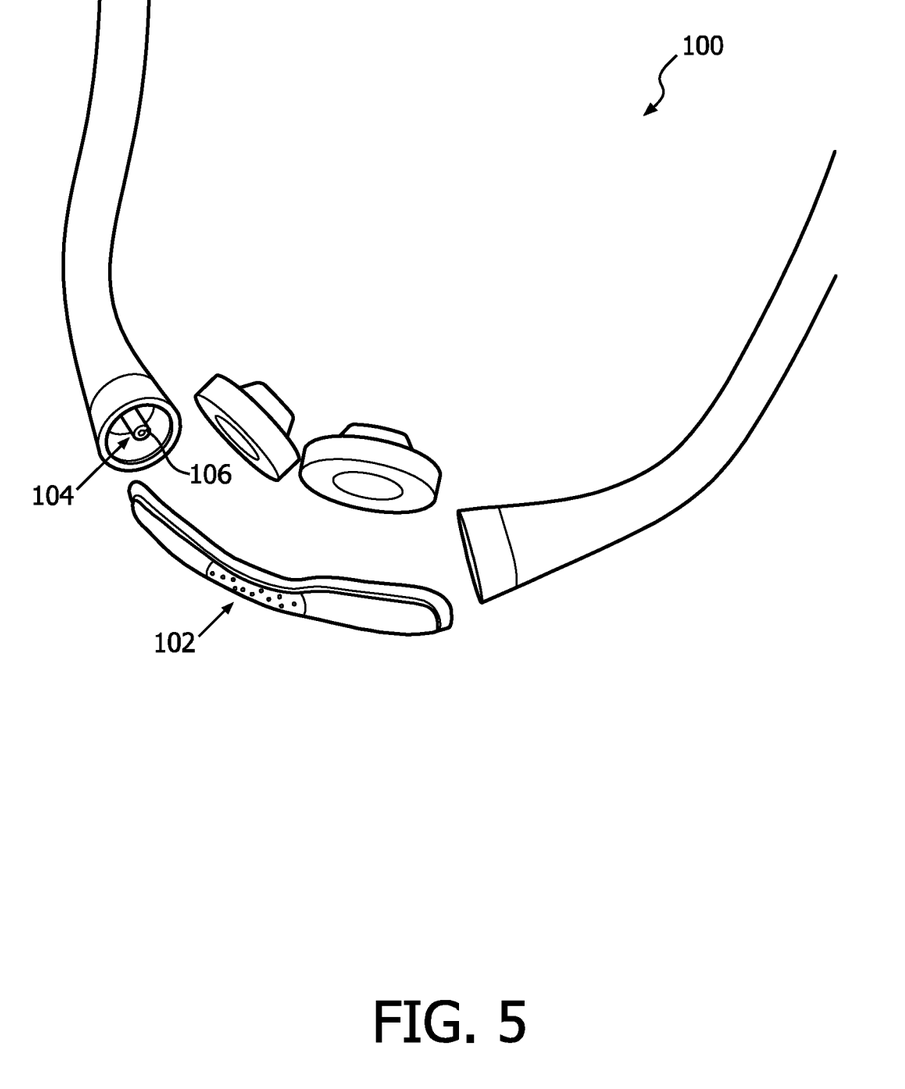
FIG. 5 is an enlarged view of a portion of the patient interface device of FIG. 1, and shown with a portion of a sealing element removed in order to see hidden features.

FIG. 5 shows a portion of patient interface device 100, with a portion of sealing element 102 removed. As shown, first end 106 is in fluid communication with an interior of sealing element 102. Although the disclosed concept is being described in association with first end 106 being in fluid communication with the interior of sealing element 102, it will be appreciated that any suitable alternative sealing element (e.g., without limitation, a nasal mask, a nasal/oral mask, and/or a full face mask) (not shown) may be employed in place of sealing element 102 in order to perform the desired function of receiving the breathing gas from gas flow generator 4 (FIG. 1) and delivering the breathing gas to the airway of patient 6, without departing from the scope of the disclosed concept.

Figure 6:
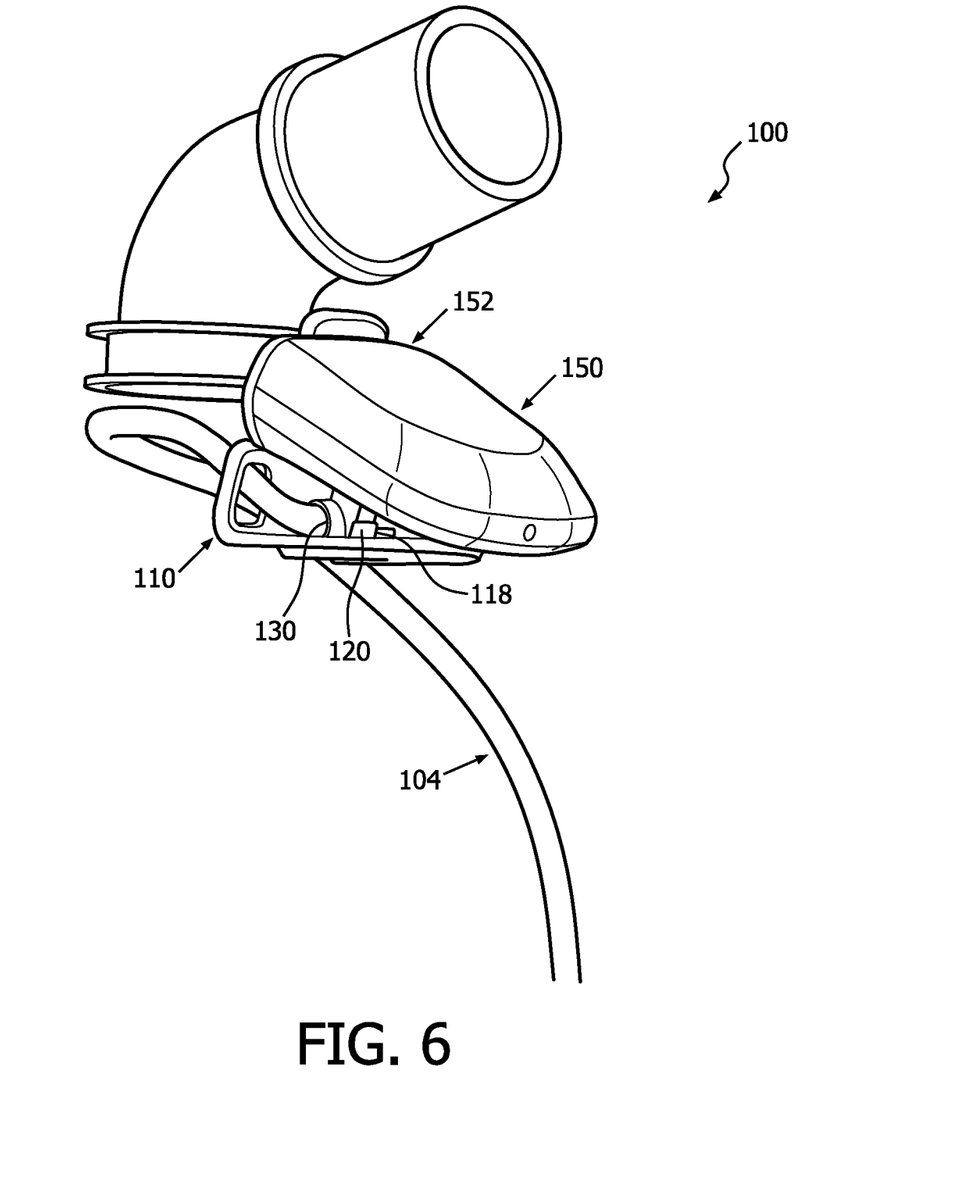
FIG. 6 is another enlarged view of a portion of the patient interface device of FIG. 1, and shown with a portion of the patient interface device removed in order to see hidden features.

Referring to FIG. 6, pressure sensor 150 is structured to measure pressure of the gas exiting second end 108 (FIG. 4) proximate the airway of patient 6 (FIG. 1). Specifically, some of the gas entering patient interface device 100 from gas flow generator 4 (FIG. 1) enters first end 106 and exits second end 108 in order to allow pressure sensor 150 to monitor pressure of gas near the airway of patient 6. However, undesirable liquid (e.g., water) often enters lumen 104, such as for example, when patient interface device 100 is cleaned. In accordance with the disclosed concept, and as will be described in greater detail hereinbelow, patient interface device 100 advantageously allows the undesirable liquid to exit patient interface device 100 so that pressure sensor 150 can take significantly more accurate pressure readings of the gas exiting second end 108, thereby allowing better pressure support therapy to be delivered to patient 6 (FIG. 1).

Figure 7:
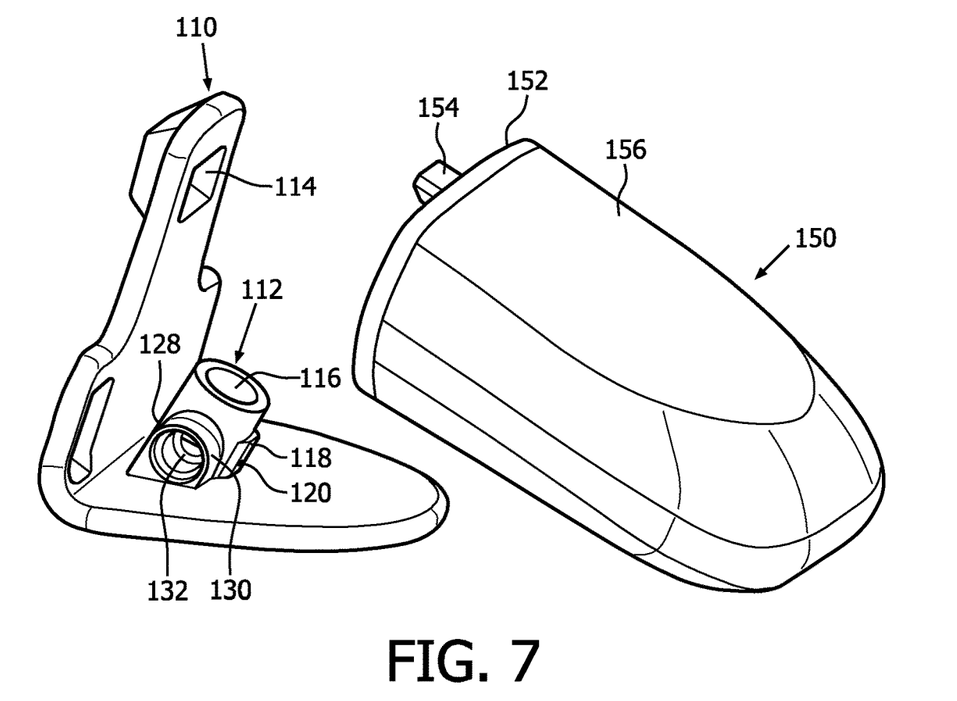
FIG. 7 is a partially exploded view of a pressure sensor and a connector member for the patient interface device of FIG. 1.
Figure 16:
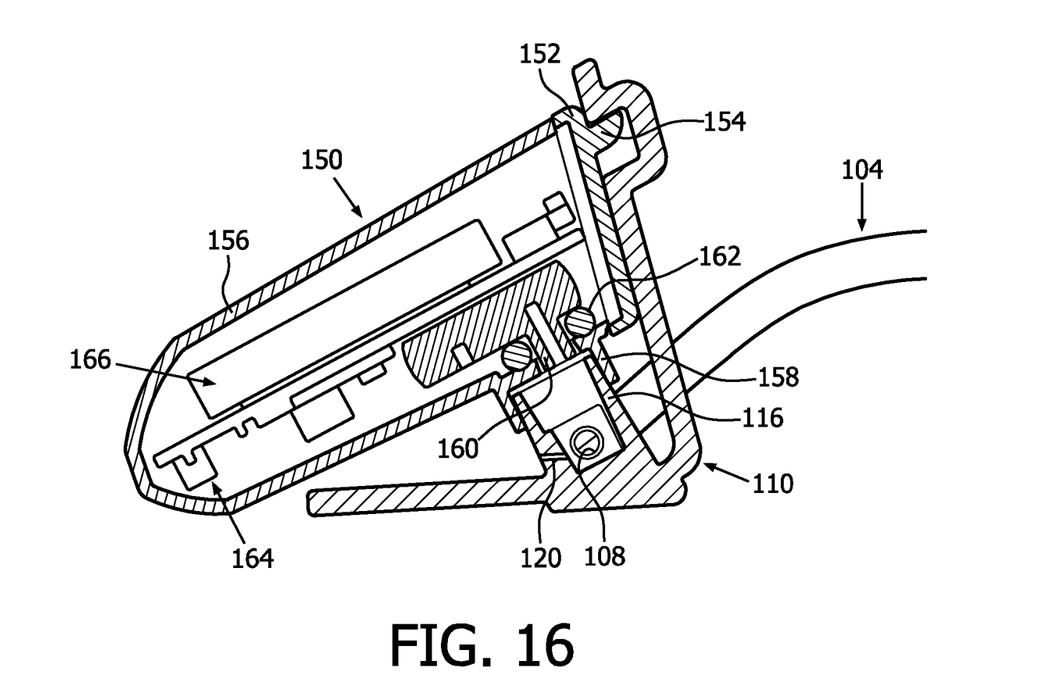
FIG. 16 is a section view of the portion of the patient interface device of FIG. 15, taken along line B-B of FIG. 15.

FIG. 7 shows connector member 110 and pressure sensor 150. Connector member 110 includes a first coupling portion 112 and a second coupling portion (i.e., grooved region 114). Pressure sensor 150 includes a cap member 152 that has a tongue 154, a housing 156, and a port (see port 158 in FIG. 16 and FIG. 17). Referring to FIG. 16, pressure sensor 150 further includes a sensing component 160, an O-ring 162 that provides a seal between sensing component 160 and housing 156, an antenna (e.g., without limitation, BLUETOOTH® antenna 164) that wirelessly transfers pressure readings to gas flow generator 4 (FIG. 1), and a power source (e.g., without limitation, battery 166). Housing 156 houses and thereby protects sensing component 160, BLUETOOTH® antenna 164, and battery 166. Port 158 (FIG. 16 and FIG. 17) allows delivery of gas to sensing component 160 (FIG. 16). Grooved region 114 is coupled to tongue 154 by a snap-fit mechanism. First coupling portion 112 includes a tubular-shaped body portion 116 that is received within (i.e., coupled to) port 158 (FIG. 16 and FIG. 17) of pressure sensor 150 by a press-fit mechanism. By having the two locations for coupling, and by employing the snap-fit and press-fit mechanisms, pressure sensor 150 is advantageously well retained on connector member 110. As a result, pressure readings can be taken from the gas exiting lumen 104, which is also coupled to first coupling portion 112.

Figure 8:
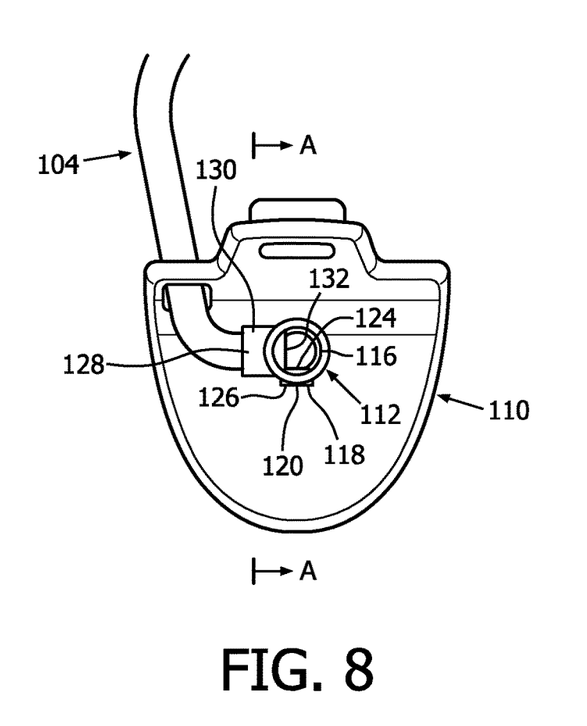
FIG. 8 is a top plan view of the connector member and the lumen for the patient interface device of FIG. 1.

First coupling portion 112 further includes a wall 118 and a receiving portion 128. Referring to FIG. 8, wall 118 has a first planar portion 124 and a second planar portion located 126 opposite and substantially parallel to first planar portion 124. First planar portion 124 is located generally internal with respect to body portion 116, and second planar portion 126 is located generally external with respect to body portion 116. Thus, wall 118 extends from a location located internal with respect to body portion 116 to a location located external with respect to body portion 116.

Figure 9:
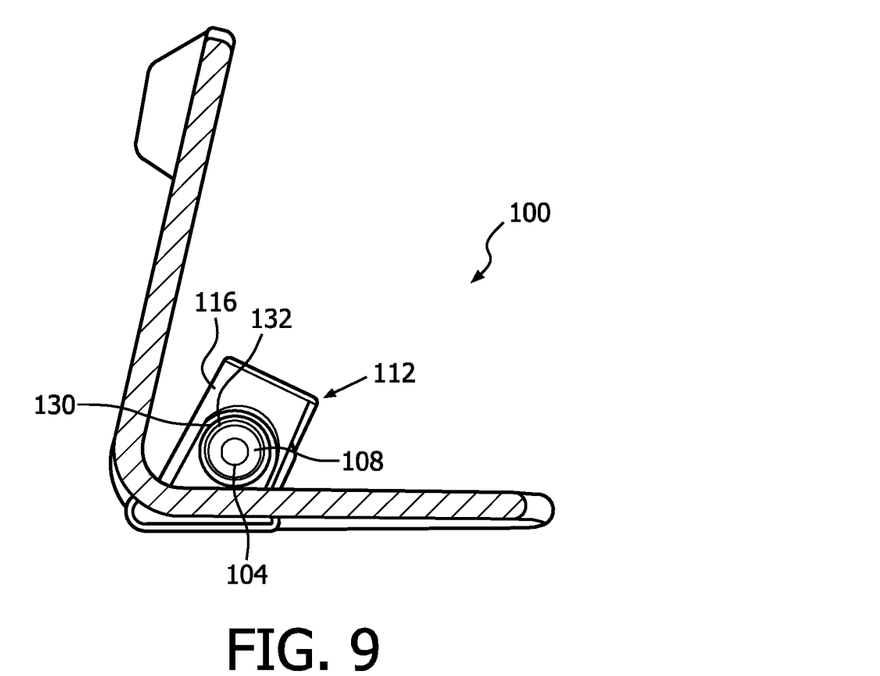
FIG. 9 is a side elevation view of the connector member and the lumen, taken along line A-A of FIG. 8.
Figure 10:
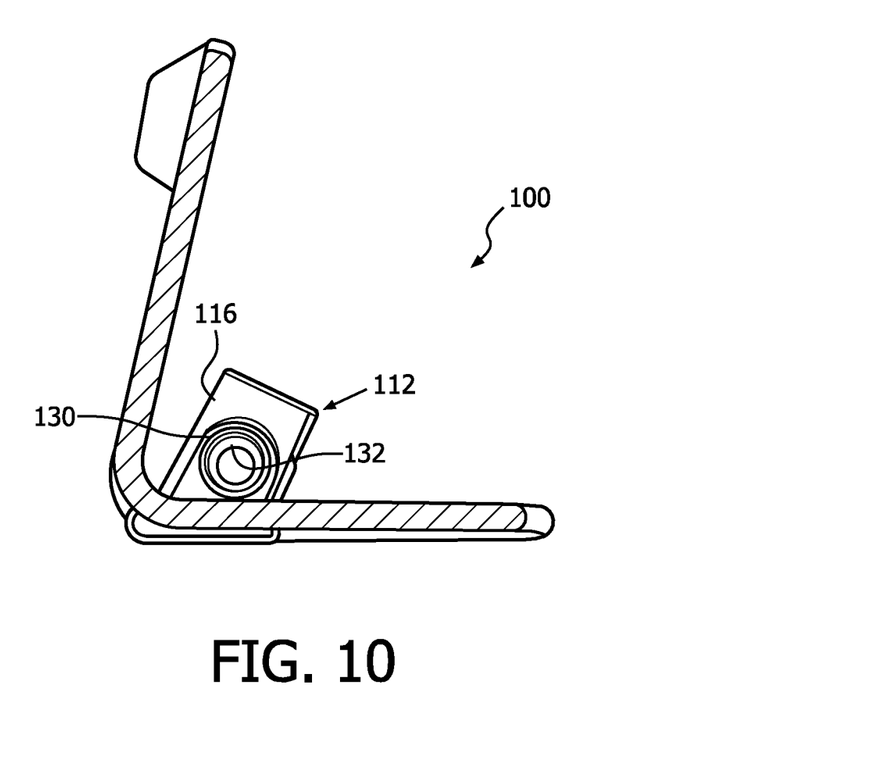
FIGS. 10-14 are different views of the connector member for the patient interface device of FIG. 1.
Figure 11:
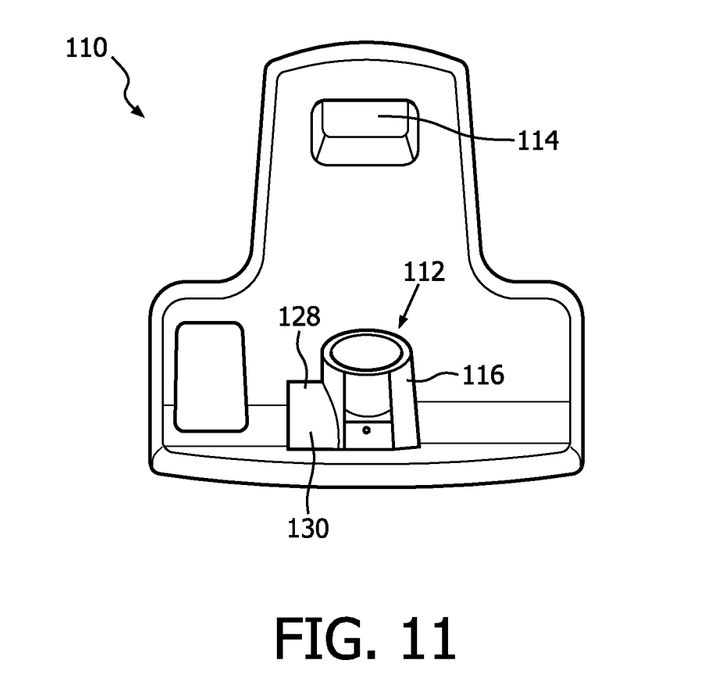
Figure 12:
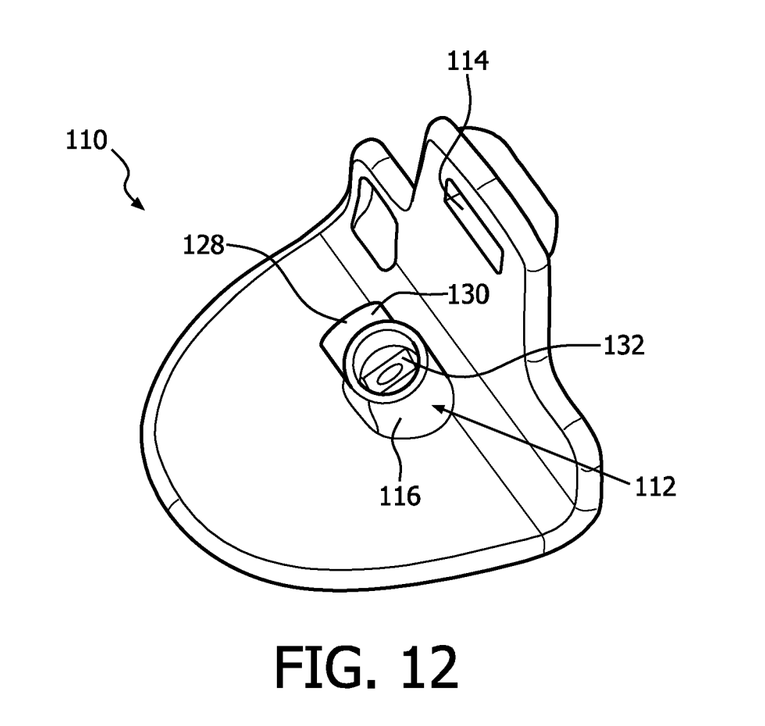

Referring again to FIG. 7, receiving portion 128, which includes a tubular portion 130 and a blocking portion 132, receives second end 108 (FIG. 4) of lumen 104 (FIG. 4). Receiving portion 128 extends from a location located internal body portion 116 to a location located external body portion 116. Specifically, tubular portion 130 is located generally external with respect to body portion 116, and blocking portion 132 is located generally internal with respect to body portion 116. Lumen 104, shown in FIG. 8, extends through tubular portion 130 and, as shown in FIG. 9, second end 108 engages blocking portion 132 in order to be maintained at a location located internal body portion 116.

FIGS. 10-14 show different views of connector member 110. Connector member 110 is preferably, but without limitation, made of a single piece of material, thereby simplifying manufacturing and reducing cost. For example, connector member 110 (i.e., grooved region 114, body portion 116, wall 118, receiving portion 128, and the remaining portions of connector member 110) may be a thermoplastic member made by an injection molding process.

Figure 13:
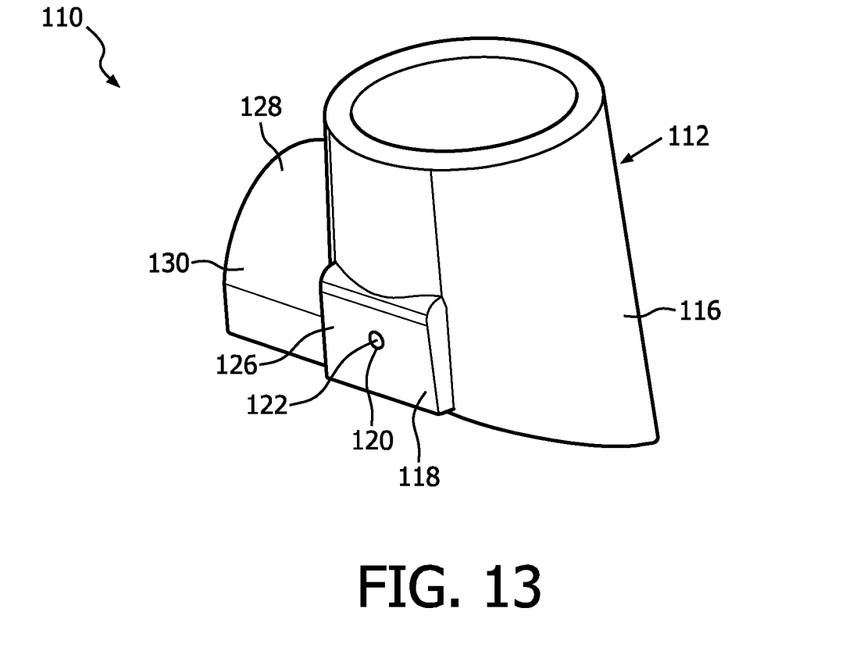
Figure 14:
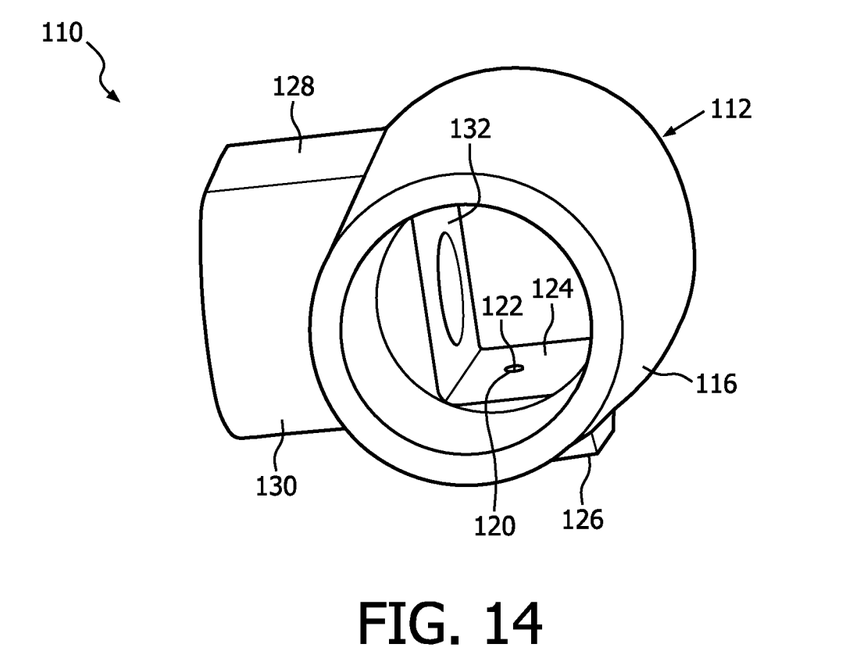

As shown in the enlarged views of FIGS. 13 and 14, wall 118 has a cylindrical-shaped surface 120 that defines a thru hole 122. Surface 120, and thus thru hole 122, extends from first planar portion 124 to second planar portion 126. As mentioned above, second end 108 of lumen 104 engages blocking portion 132, which is located internal with respect to body portion 116. As a result, gas passes through blocking portion 132 and enters body portion 116 in order that pressure sensor 150, which is coupled to body portion 116, can sense pressure.

Moreover, because surface 120 extends from first planar portion 124 (i.e., a location also located internal body portion 116), a flow of gas is created from an interior of body portion 116 through thru hole 122 to an exterior of body portion 116. In this manner, novel flow through thru hole 122 is utilized to allow undesirable liquid located within lumen 104 to advantageously escape patient interface device 100. Stated differently, thru hole 122 is a weep hole through which the liquid can exit patient interface device 100, rather than being trapped inside and compromising pressure readings. In other words, when the undesirable liquid exits patient interface device 100 through thru hole 122, a pressure of gas that is more similar to the pressure at first end 106 is ultimately able to enter pressure sensor 150. That is, the gas experiences significantly less resistance (e.g., a resistance that would have been, but is not present in the instant invention, due to the surface tension of the liquid on the wall of lumen 104) passing through lumen 104. As a result, pressure readings in patient interface device 100 are advantageously more accurate, which allows pressure support therapy delivered to patient 6 (FIG. 1) to be better controlled and therefore improved.

Figure 15:
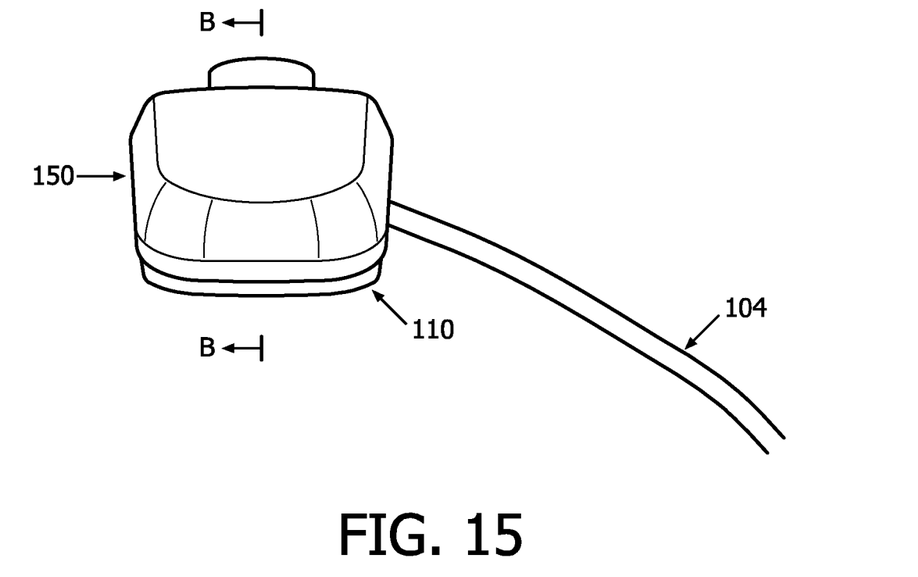
FIG. 15 is a rear view of a portion of the patient interface device of FIG. 1, and shown with a portion of the patient interface device removed in order to see hidden features.
Figure 17:
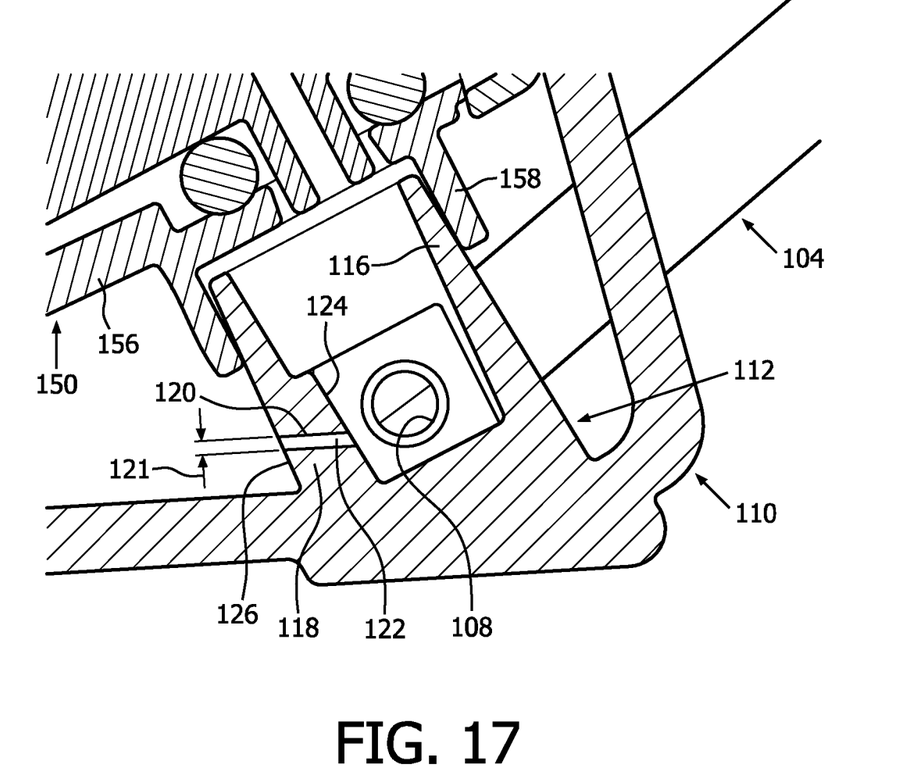
FIG. 17 is an enlarged view of the section view of FIG. 16.

FIGS. 15-17 show lumen 104, connector member 110, and pressure sensor 150. As shown in FIG. 16 and FIG. 17, body portion 116 extends into pressure sensor 150. Furthermore, and referring to FIG. 17, because first planar portion 124 and second planar portion 126 are substantially parallel, the length of cylindrical-shaped surface 120 is advantageously able to be consistent (i.e., and is equal to the perpendicular distance from first planar portion 124 to second planar portion 126). Specifically, if surface 120 were to inadvertently be cut in a slightly different position (not shown) through wall 118, the length of such a surface would still be the same as the length of surface 120. In this manner, the effective pressure drop created due to thru hole 122 can be consistently accounted for (i.e., offset) by pressure sensor 150.

Additionally surface 120 has a diameter 121 (FIG. 17) that is preferably greater than 0.007 inches, more preferably being about 0.013 inches. Having diameter 121 this length advantageously allows undesirable liquid to escape, yet provides a relatively small pressure drop so that the accuracy of pressure readings is not significantly affected. It will however be appreciated that a surface (not shown) may have any known or suitable alternative diameter depending on the pressure of the gas. Furthermore, surface 120 is preferably cut by a laser-cutting apparatus, which advantageously allows the length (i.e., the perpendicular distance between first planar portion 124 and second planar portion 126) and diameter 121 of surface 122 to be consistent, also causing the associated pressure drop to be minimized. It will, however, be appreciated that surface 120 can be cut by any suitable alternative known cutting apparatus and/or mechanism in order to create the desired size and shape of surface 120.

Figure 18:
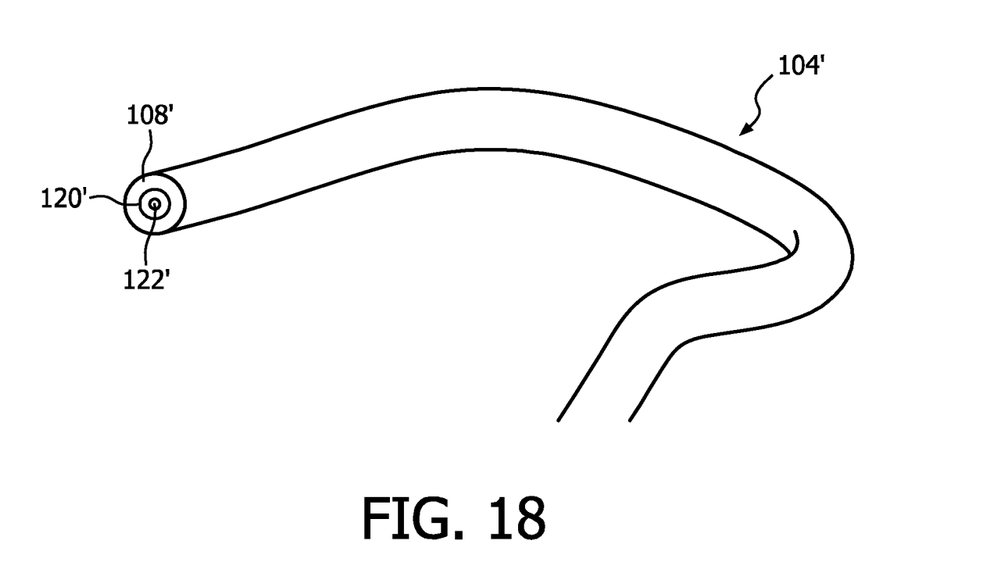
FIG. 18 is an isometric view of a portion of a lumen, in accordance with another non-limiting embodiment of the disclosed concept.

FIG. 18 shows a portion of another lumen 104' that may be employed in patient interface device 100 instead of lumen 104. As shown, lumen 104' has a second end 108' and a cylindrical-shaped surface 120' that defines a thru hole 122' extending through lumen 104' proximate second end 108'. Thus, although the disclosed concept has been described in association with thru hole 122 in connector member 110, it will be appreciated that novel flow to allow undesirable liquid within patient interface device 100 to escape can be provided by surface 120' on lumen 104' instead of surface 120 on connector member 110. Benefits, such as more accurate pressure readings and better controlled pressure support therapy, associated with surface 120 in connector member 110 likewise apply to surface 120' on lumen 104'. Additionally, the diameter of surface 120', like diameter 121, is preferably between 0.008 and 0.018 inches, more preferably being about 0.013 inches, which advantageously allows the undesirable liquid to escape (i.e., to weep out of) patient interface device 100 and not cause a significantly undesirable pressure drop.

It will be appreciated that a method of removing undesirable liquid in patient interface device 100 includes the steps of producing the flow of breathing gas to be delivered through sealing element 102 to the airway of patient 6 with gas flow generator (4); and forcing undesirable liquid in lumen 104,104' through thru hole 122,122' with a portion of the gas exiting lumen 104,104' proximate second end 108, 108'. The method further includes the steps of providing a first pressure drop in lumen 104,104'; and providing a second pressure drop in thru hole 122,122', the second pressure drop being higher than the first pressure drop. Because the pressure drop in thru hole 122,122' is higher than the pressure drop in lumen 104,104', there is a measureable back-pressure at pressure sensor 150.

Accordingly, the disclosed concept provides for an improved pressure support system 2, and patient interface device 100 and liquid removal method therefor, which among other benefits, allows undesirable liquid in a lumen 104,104' to be removed, so that pressure readings taken by a pressure sensor 150 coupled thereto can be more accurate. As a result of having more accurate pressure readings, pressure support therapy delivered to a patient 6 can be better controlled and therefore improved.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for a pressure support system, the pressure support system comprising a gas flow generator structured to produce a flow of breathing gas to be delivered to an airway of a patient, the patient interface device comprising:
    a fluid coupling conduit structured to receive the flow of breathing gas from the gas flow generator;
    a delivery tube having a first end and a second end, wherein the first end of the delivery tube is connected to the fluid coupling conduit for receiving the flow of breathing gas from the fluid coupling conduit;
    a sealing element connected to the second end of the deliver tube for receiving the flow of breathing gas from the delivery tube, the sealing element being structured to engage a face of the patient;
    a lumen distinct from and located inside the deliver tube, the lumen having a first end and a second end opposite and distal the first end of the lumen, the first end of the lumen being in fluid communication with an interior of the sealing element;
    a connector member separate from the fluid coupling conduit, wherein the second end of the lumen is directly connected to the connector member;
    a pressure sensor directly connected to the connector member, the pressure sensor being structured to sense pressure of the breathing gas exiting the second end of the lumen; and
    a surface provided on the connector member, the surface defining a thru hole through which liquid in the lumen can escape, wherein the connector member comprises a first coupling portion and a second coupling portion each coupled to the pressure sensor, wherein the surface is provided on the first coupling portion, wherein the first coupling portion is coupled to the pressure sensor by a press-fit mechanism, wherein the second coupling portion is coupled to the pressure sensor by a snap-fit mechanism, and wherein the pressure sensor comprises a cap member having a tongue; and wherein the second coupling portion is a grooved region coupled to the tongue by a snap-fit mechanism.

2. The patient interface device of claim 1, wherein the first coupling portion comprises a tubular-shaped body portion; and wherein the body portion extends into the pressure sensor.

3. The patient interface device of claim 2, wherein the first coupling portion further comprises a wall having the surface defining the thru hole; and wherein the wall extends from a location disposed internal the body portion to a location disposed external the body portion.

4. The patient interface device of claim 3, wherein the wall comprises a first planar portion and a second planar portion opposite and substantially parallel to the first planar portion; wherein the first planar portion is disposed internal the body portion; wherein the second planar portion is disposed external the body portion; and wherein the surface extends from the first planar portion to the second planar portion.

5. The patient interface device of claim 3, wherein the wall and the body portion are made of a single piece of material.

6. The patient interface device of claim 3 wherein the surface is cylindrical-shaped.

7. The patient interface device of claim 2, wherein the first coupling portion further comprises a receiving portion that receives the second end of the lumen; and wherein the receiving portion extends from a location disposed internal the body portion to a location disposed external the body portion.

8. A patient interface device for a pressure support system, the pressure support system comprising a gas flow generator structured to produce a flow of breathing gas to be delivered to an airway of a patient, the patient interface device comprising:
    a fluid coupling conduit structured to receive the flow of breathing gas from the gas flow generator;
    a delivery tube having a first end and a second end, wherein the first end of the delivery tube is connected to the fluid coupling conduit for receiving the flow of breathing gas from the fluid coupling conduit;
    a sealing element connected to the second end of the deliver tube for receiving the flow of breathing gas from the delivery tube, the sealing element being structured to engage a face of the patient;
    a lumen distinct from and located inside the deliver tube, the lumen having a first end and a second end opposite and distal the first end of the lumen, the first end of the lumen being in fluid communication with an interior of the sealing element,
    a connector member separate from the fluid coupling conduit, wherein the second end of the lumen is directly connected to the connector member;
    a pressure sensor directly connected to the connector member, the pressure sensor being structured to sense pressure of the breathing gas exiting the second end of the lumen, and
    a surface provided on the connector member, the surface defining a thru hole through which liquid in the lumen can escape, wherein the first coupling portion comprises a tubular-shaped body portion, wherein the connector member comprises a first coupling portion and a second coupling portion each coupled to the pressure sensor, wherein the surface is provided on the first coupling portion, wherein the body portion extends into the pressure sensor, wherein the first coupling portion further comprises a receiving portion that receives the second end of the lumen; and wherein the receiving portion extends from a location disposed internal the body portion to a location disposed external the body portion, and wherein the receiving portion comprises a second tubular portion and a blocking portion; wherein the second tubular portion is disposed external the body portion; wherein the blocking portion is disposed internal the body portion; wherein the lumen extends through the second tubular portion; and wherein the second end of the lumen engages the blocking portion in order to be maintained at the location disposed internal the body portion.

9. The patient interface device of claim 8, wherein the receiving portion and the body portion are made of a single piece of material.

10. A pressure support system, comprising:
(a) a gas flow generator structured to produce a flow of breathing gas to be delivered to an airway of a patient; and
(b) a patient interface device comprising:
a fluid coupling conduit structured to receive the flow of breathing gas from the gas flow generator;
a delivery tube having a first end and a second end, wherein the first end of the delivery tube is connected to the fluid coupling conduit for receiving the flow of breathing gas from the fluid coupling conduit;
a sealing element connected to the second end of each delivery tube for receiving the flow of breathing gas from each delivery tube, the sealing element being structured to engage a face of the patient;
a lumen distinct from and located inside the delivery tube, the lumen having a first end and a second end opposite and distal the first end of the lumen, the first end of the lumen being in fluid communication with an interior of the sealing element;
a connector member separate from the fluid coupling conduit, wherein the second end of the lumen is directly connected to the connector member;
a pressure sensor directly connected to the connector member, the pressure sensor being structured to sense pressure of the breathing gas exiting the second end of the lumen; and
a surface provided on the connector member, the surface defining a thru hole through which liquid in the lumen can escape, wherein the first coupling portion comprises a tubular-shaped body portion, wherein the connector member comprises a first coupling portion and a second coupling portion each coupled to the pressure sensor; wherein the surface is provided on the first coupling portion, wherein the body portion extends into the pressure sensor, wherein the first coupling portion further comprises a receiving portion that receives the second end of the lumen; and wherein the receiving portion extends from a location disposed internal the body portion to a location disposed external the body portion, and wherein the receiving portion comprises a second tubular portion and a blocking portion; wherein the second tubular portion is disposed external the body portion; wherein the blocking portion is disposed internal the body portion; wherein the lumen extends through the second tubular portion; and wherein the second end of the lumen engages the blocking portion is in order to be maintained at the location disposed internal the body portion.

11. A method of removing liquid in a patient interface device comprising a fluid coupling conduit structured to receive a flow of breathing gas from a gas flow generator; a delivery tube having a first end and a second end, wherein the first end of the delivery tube is connected to the fluid coupling conduit for receiving the flow of breathing gas from the fluid coupling conduit; a sealing element connected to the second end of each delivery tube for receiving the flow of breathing gas from each delivery tube, the sealing element being structured to engage a face of a patient; a lumen distinct from and located inside the delivery tube, the lumen having a first end and a second end opposite and distal the first end of the lumen, the first end of the lumen being in fluid communication with an interior of the sealing element; a connector member separate from the fluid coupling conduit, wherein the second end of the lumen is directly connected to the connector member; a pressure sensor directly connected to the connector member, the pressure sensor being structured to sense pressure of the breathing gas exiting the second end of the lumen; and a surface provided on the connector member, the surface defining a thru hole, wherein the first coupling portion comprises a tubular-shaped body portion, wherein the connector member comprises a first coupling portion and a second coupling portion each coupled to the pressure sensor; wherein the surface is provided on the first coupling portion, wherein the body portion extends into the pressure sensor, wherein the first coupling portion further comprises a receiving portion that receives the second end of the lumen; and wherein the receiving portion extends from a location disposed internal the body portion to a location disposed external the body portion, and wherein the receiving portion comprises a second tubular portion and a blocking portion; wherein the second tubular portion is disposed external the body portion, wherein the blocking portion is disposed internal the body portion; wherein the lumen extends through the second tubular portion; and wherein the second end of the lumen engages the blocking portion in order to be maintained at the location disposed internal the body portion, the method comprising the steps of:
producing the flow of breathing gas to be delivered through the sealing element to an airway of the patient with the gas flow generator; and
forcing liquid in the lumen through the thru hole with a portion of the gas exiting the lumen proximate the second end of the lumen.

12. The method of claim 11, further comprising the steps of:
providing a first pressure drop in the lumen; and
providing a second pressure drop in the thru hole, the second pressure drop being higher than the first pressure drop.

* * * * *